(12) United States Patent
Molz, IV et al.

(10) Patent No.: US 7,794,481 B2
(45) Date of Patent: Sep. 14, 2010

(54) FORCE LIMITING COUPLING ASSEMBLIES FOR SPINAL IMPLANTS

(75) Inventors: Fred J. Molz, IV, Collierville, TN (US); Jeff R. Justis, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 319 days.

(21) Appl. No.: 11/112,221

(22) Filed: Apr. 22, 2005

(65) Prior Publication Data

US 2006/0241595 A1 Oct. 26, 2006

(51) Int. Cl.
*A61B 17/70* (2006.01)
(52) U.S. Cl. .................................................. 606/270
(58) Field of Classification Search .................. 606/61, 606/72–73, 246, 250–253, 257, 265–272
See application file for complete search history.

(56) References Cited

U.S. PATENT DOCUMENTS

| | | | |
|---|---|---|---|
| 4,569,338 A | 2/1986 | Edwards | |
| 4,827,918 A | 5/1989 | Olerud | |
| 5,047,029 A | 9/1991 | Aebi et al. | |
| 5,053,034 A | 10/1991 | Olerud | |
| 5,176,680 A | 1/1993 | Vignaud et al. | |
| 5,190,543 A | 3/1993 | Schlapfer | |
| 5,234,431 A | 8/1993 | Keller | |
| 5,254,118 A | 10/1993 | Mirkovic | |
| 5,261,909 A | 11/1993 | Sutterlin et al. | |
| 5,282,801 A | 2/1994 | Sherman | |
| 5,443,467 A * | 8/1995 | Biedermann et al. | ........... 606/65 |
| 5,527,314 A | 6/1996 | Brumfield et al. | |
| 5,534,002 A | 7/1996 | Brumfield et al. | |
| 5,545,166 A | 8/1996 | Howland | |
| 5,562,662 A | 10/1996 | Brumfield | |
| 5,569,247 A | 10/1996 | Morrison | |
| 5,591,166 A | 1/1997 | Bernhardt et al. | |
| 5,624,441 A | 4/1997 | Sherman et al. | |
| 5,628,740 A | 5/1997 | Mullane | |
| 5,643,263 A | 7/1997 | Simonson | |
| 5,725,528 A | 3/1998 | Errico et al. | |
| 5,735,851 A | 4/1998 | Errico et al. | |
| 5,782,833 A * | 7/1998 | Haider | ........................ 606/61 |
| 5,800,435 A | 9/1998 | Errico et al. | |

(Continued)

FOREIGN PATENT DOCUMENTS

WO WO 98/12976 4/1998

(Continued)

OTHER PUBLICATIONS

TiMX Comprehensive Low Back System, DePuy AcroMed, © 1999.

(Continued)

*Primary Examiner*—Thomas C Barrett
*Assistant Examiner*—Michael J Araj

(57) ABSTRACT

The forces exerted on a spinal implant by one or more coupling assemblies are controlled to facilitate the use of the implant in spinal stabilization and other procedures. The coupling assemblies are structured to limit the forces exerted on the implant to avoid undesirable alteration of a characteristic of the implant while engaging the implant to the coupling assembly and providing at least one of a rigid, semi-rigid or variable engagement of the coupling assembly with one or more anatomical structures of the spinal column.

23 Claims, 4 Drawing Sheets

U.S. PATENT DOCUMENTS

| | | | |
|---|---|---|---|
| 5,885,285 | A | 3/1999 | Simonson |
| 5,885,286 | A * | 3/1999 | Sherman et al. ............... 606/61 |
| 5,904,683 | A | 5/1999 | Pohndorf et al. |
| 5,910,142 | A | 6/1999 | Tatar |
| 5,938,663 | A | 8/1999 | Petreto |
| 5,947,967 | A | 9/1999 | Barker |
| 6,010,503 | A | 1/2000 | Richelsoph et al. |
| 6,010,504 | A | 1/2000 | Rogozinski |
| 6,050,997 | A | 4/2000 | Richelsoph |
| 6,063,090 | A | 5/2000 | Schlapfer |
| 6,113,601 | A | 9/2000 | Tatar |
| 6,132,432 | A | 10/2000 | Mullane |
| 6,183,473 | B1 | 2/2001 | Ashman |
| 6,187,005 | B1 | 2/2001 | Brace et al. |
| 6,210,413 | B1 | 4/2001 | Justis |
| 6,248,105 | B1 * | 6/2001 | Schlapfer et al. ............... 606/61 |
| 6,248,107 | B1 | 6/2001 | Foley |
| 6,267,765 | B1 | 7/2001 | Taylor et al. |
| 6,296,642 | B1 | 10/2001 | Morrison et al. |
| 6,315,779 | B1 | 11/2001 | Morrison et al. |
| 6,352,537 | B1 | 3/2002 | Strnad |
| 6,355,038 | B1 | 3/2002 | Pisharodi |
| 6,478,798 | B1 | 11/2002 | Howland |
| 6,485,491 | B1 | 11/2002 | Farris et al. |
| 6,520,962 | B1 | 2/2003 | Taylor et al. |
| 6,524,315 | B1 | 2/2003 | Selvitelli et al. |
| 6,547,790 | B2 | 4/2003 | Harkey, III et al. |
| 6,562,038 | B1 | 5/2003 | Morrison |
| 6,565,565 | B1 | 5/2003 | Yuan et al. |
| 6,626,906 | B1 | 9/2003 | Young |
| 6,685,705 | B1 | 2/2004 | Taylor et al. |
| 6,770,075 | B2 | 8/2004 | Howland |
| 6,783,527 | B2 | 8/2004 | Drewry et al. |
| 6,835,196 | B2 * | 12/2004 | Biedermann et al. .......... 606/61 |
| 6,896,677 | B1 * | 5/2005 | Lin ........................... 606/266 |
| 7,066,937 | B2 | 6/2006 | Shluzas |
| 7,087,057 | B2 | 8/2006 | Konieczynski et al. |
| 2002/0082602 | A1 * | 6/2002 | Biedermann et al. .......... 606/61 |
| 2002/0133159 | A1 | 9/2002 | Jackson |
| 2003/0100896 | A1 | 5/2003 | Biedermann et al. |
| 2003/0100904 | A1 * | 5/2003 | Biedermann ................. 606/73 |
| 2003/0125741 | A1 * | 7/2003 | Biedermann et al. .......... 606/61 |
| 2003/0149431 | A1 | 8/2003 | Varieur |
| 2003/0153911 | A1 | 8/2003 | Shluzas |
| 2003/0167058 | A1 * | 9/2003 | Shluzas ....................... 606/61 |
| 2004/0176766 | A1 | 9/2004 | Shluzas |
| 2005/0240180 | A1 | 10/2005 | Vienney et al. |
| 2007/0055244 | A1 | 3/2007 | Jackson |
| 2007/0161999 | A1 | 7/2007 | Biedermann et al. |
| 2007/0167949 | A1 | 7/2007 | Altarac et al. |
| 2008/0154315 | A1 | 6/2008 | Jackson |
| 2008/0215100 | A1 | 9/2008 | Matthis et al. |

FOREIGN PATENT DOCUMENTS

| | | |
|---|---|---|
| WO | WO 03/024343 | 3/2003 |
| WO | WO 2005/102195 | 11/2005 |

OTHER PUBLICATIONS

Pass® Deformity System, Encore Surgical, © Jan. 2002.

Spine Internal Fixation Device, Encore Surgical, © Jan. 2002.

* cited by examiner

FORCE LIMITING COUPLING ASSEMBLIES FOR SPINAL IMPLANTS

BACKGROUND

Spinal implants can be engaged to or along one or more vertebrae of the spinal column for the treatment of various spinal conditions. Fasteners can be provided to secure the implant to a particular location along the spinal column. The engagement between the implant and the fasteners can result in forces being exerted on the implant. In some cases, one or more characteristics of the implant could be altered as a result of these forces.

SUMMARY

The forces exerted on a spinal implant by one or more coupling assemblies are controlled to facilitate the application of implants having characteristics that may be undesirably altered if sufficient forces are exerted thereon as a result of spinal stabilization and other procedures. The coupling assemblies are structured to limit the forces exerted on the implant by the coupling assembly while providing at least one of a rigid, semi-rigid or variable engagement of the coupling assembly with one or more anatomical structures of the spinal column.

The coupling assemblies secure one or more implants along the spinal column while providing a limited or controlled exertion of forces by the coupling assembly on the implant. The coupling assemblies include an anchor member for engaging the coupling assembly to an underlying bony structure, a receiver member for receiving an implant, and a securing member for securing the implant to the receiver member. The coupling assemblies each include a force limiting construct that secures the implant to the coupling assembly while limiting or controlling the forces applied to the implant as the anchor member is engaged in a position relative to the coupling assembly with the securing member.

DETAILED DESCRIPTION OF THE ILLUSTRATED EMBODIMENTS

Figure 1:
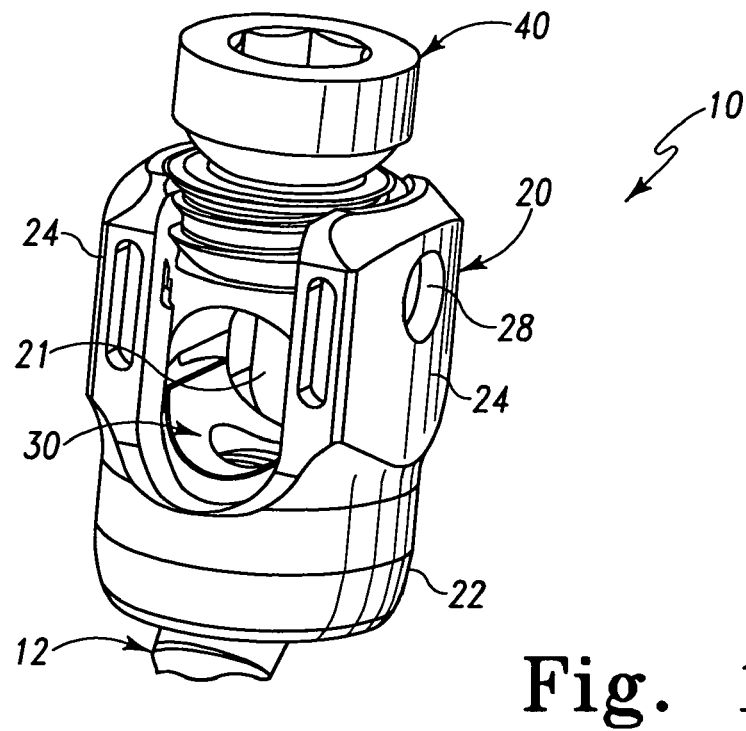
FIG. 1 is a perspective view of one embodiment coupling assembly.
Figure 2:
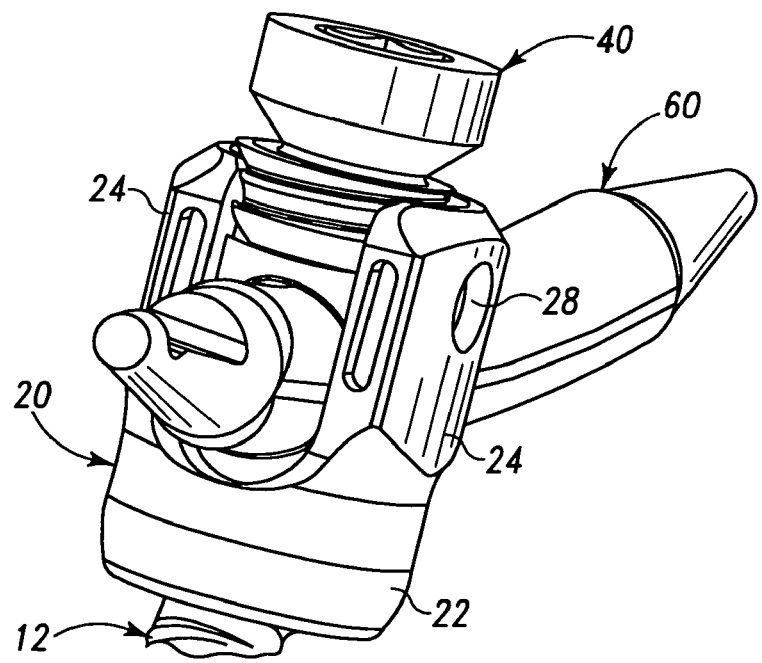
FIG. 2 is the coupling assembly of FIG. 1 with an implant positioned for engagement with the coupling assembly.
Figure 3A:
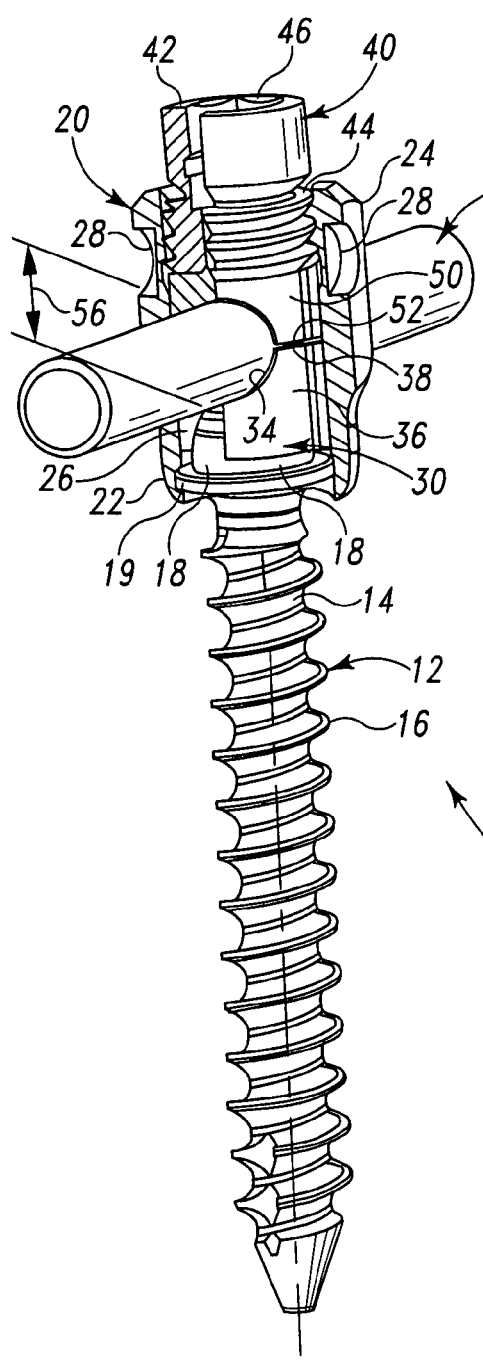
FIGS. 3A and 3B are partial sectional views of the coupling assembly of FIG. 1 with an implant extending therethrough and an anchor member extending therefrom.
Figure 3B:
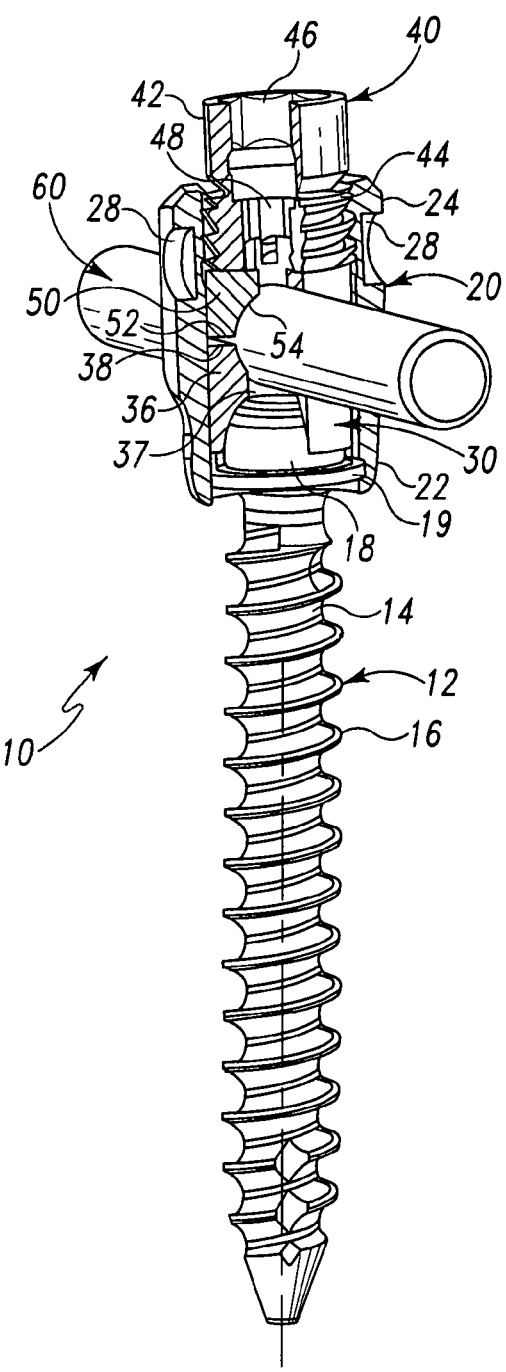

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Coupling assemblies are provided to secure one or more implants along the spinal column while providing a limited or controlled exertion of forces by the coupling assembly on the implant. The coupling assemblies each include an anchor member for engaging the coupling assembly to an underlying bony structure, a receiver member for receiving the implant, and a securing member for securing the implant to the receiver member. The coupling assemblies each include a force limiting construct that interacts with the securing member securing the implant to the coupling assembly to limit or control the forces applied to the implant. The limitation on the forces exerted on the implant prevents undesirable alteration of a characteristic of the implant.

Referring to FIGS. 1-3B, there is shown a coupling assembly 10 including an anchor member 12, a receiver member 20 coupled to anchor member 12, and a securing member 40. An implant 60 is positionable on, in or about receiver member 20, and securing member 40 is movable relative to implant 60 and receiver member 20 to secure implant 60 to coupling assembly 10. Coupling assembly 10 includes a force limiting construct that limits or controls the forces applied to implant 60 by receiver member 20 and securing member 40 when implant 60 is secured to coupling assembly 10. The implant can be engaged along one or more vertebrae of the spinal column with one or more coupling assemblies 10 or any other type of fastener to provide, for example, a spinal stabilization system.

Securing member 40 is movably engageable with receiver member 20 and includes an upper break-off portion 42 and a lower engaging portion 44. Lower engaging portion 44 is illustrated as an externally threaded set screw, although other configurations are contemplated. A first tool recess 46 is formed by break-off portion 42, and a second tool recess 48 is formed by engaging portion 44. A driving tool in first tool recess 46 can be manipulated to engage securing member 40 in receiver member 20 in firm engagement until sufficient resistance is supplied to cause a torque to be applied to break-off portion 42 to remove it. Second tool recess 48 is accessible to allow a tool to be positioned to apply force to tighten or loosen securing member 40 even when break-off portion 42 is removed. Securing member 40 further comprises lower extensions 50 that are rotatable relative to engaging portion 44. Accordingly, as engaging portion is threadingly engaged along arms 24, lower extensions 50 can advance linearly toward and along the opposite sides of implant 60. Each of the lower extensions 50 includes an end surface 52. An implant engaging surface 54 extends between lower extensions 50. In the illustrated embodiment, implant engaging surface 54 is concavely curved, and other shapes are also contemplated.

Receiver member 20 includes a lower portion 22 and opposing arms 24 extending therefrom that define an implant receiving portion 21 for receiving implant 60. Arms 24 each include an internal thread profile to threadingly engage securing member 40, although other engagement structures to engage securing member 40 and receiving member 20 to one another are contemplated. Arms 24 each include a through-hole 28 to receive and facilitate engagement by and manipulation with an insertion instrument (not shown.) Receiver member 20 further includes a seat member 30 positioned between arms 24 adjacent a head 18 of anchor member 12. Lower portion 22 of receiver member 20 defines a receptacle 26 in which head 18 of anchor member 12 is pivotally captured and retained with a retaining clip 19.

Seat member 30 is positioned in the adjacent implant receiving portion 21 of receiver member 20 along arms 24. A central opening 37 is provided in communication with head 18 of anchor member 12 to receive a driving tool (not shown) to apply a driving force to anchor member 12. Seat member 30 includes an implant support surface 34 defining a lower portion of implant receiving portion 21. Implant support surface 34 is defined at least in part by upper extensions 36 of seat member 30. Upper extensions 36 include an upper contact surface 38 contactable with end surfaces 52 of securing member 40. Other embodiments contemplate that one of seat member 30 and securing member 40 does not include extensions, and the other of seat member 30 and securing member 40 includes extensions of sufficient length to contact the other of seat member 30 and securing member 40.

The relationship between securing member 40 and seat member 30 when in contact with one another defines a force limiting construct that limits forces exerted on implant 60. Implant support surface 34 and implant engaging surface 54 are moveable toward one another to an implant securing position where surfaces 34, 54 are separated by a spacing 56. Spacing 56 is sized to grip implant 60 between surfaces 34, 54 with sufficient force to secure implant 60 to coupling assembly 10, but limit the exerted forces to prevent undesirable alteration of one or more characteristics of implant 60.

In use, anchor member 12 is engaged to an underlying bony structure with receiver member 20 positioned to receive implant 60. Implant 60 is positioned in implant receiving portion 21 of receiver member 20 along or adjacent implant support surface 34 of seat member 30. Securing member 40 is engaged to receiver member 20, and advanced therealong until implant engaging surface 54 contacts implant 60. Securing member 40 and seat member 30 define an implant holder in which implant engaging surface 54 is spaced a distance 56 from implant support surface 34. In this configuration, end surfaces 52 are positioned in contact with upper contact surfaces 38 of seat member 30, and this force limiting construct maintains spacing 56 and prevents it from decreasing as securing 40 is further advanced distally in receiver member 20. If securing member 40 is further advanced distally in receiver member 20, it simultaneously moves seat member 30 distally. In one embodiment, this positions seat member 30 into contact with head 18 of anchor member 12 to rigidly fix anchor member 12 in receiver member 20. Other embodiments contemplate that anchor member 12 maintains a multi-axial arrangement in receiver member 20 even when securing member 40 and seat member 30 are firmly engaged to one another such that distal movement in receiver member 20 cannot be obtained.

The maintenance of spacing 56 with the force limiting construct allows spacing 56 to be sized to provide a desired frictional or clamping engagement with implant to maintain implant 60 in position relative to coupling assembly 10, but limits the forces applied to preserve, maintain or prevent substantial alteration of one or more desired characteristics of implant 60. For example, implant 60 can be made from a polymer material, and the spacing 56 prevents securing member 40 and or seat member 30 from piercing, punching, cutting, compressing, or otherwise deforming implant 60 in an undesired fashion. The characteristic of implant 60 can include any one or combination of surface profile, cross-sectional size, cross-sectional shape, cross-sectional area, compression stress, and shear stress, for example.

Anchor member 12 in the illustrated embodiment is a bone screw and includes a shaft 14 having a thread profile 16 therealong and enlarged head 18 at a proximal end of anchor member 12. Head 18 includes a tool recess (not shown) to receive a driving tool to facilitate engagement of anchor member 12 to the underlying bone and ridges along an upper surface thereof that are engaged by seat member 30 to lock the anchor members 12 in position relative to receiver member 20. Various forms for anchor member 12 are contemplated, including threaded and non-threaded anchors, uni-axial and multi-axial arrangements, hooks, clamps, spikes, cables, interbody implants, fusion devices, cannulated screws, fenestrated screws, and bolts, for example.

Implant 60 can be structured either along or in combination with one or more other implants and/or coupling assemblies to provide a desired stabilization effect. Implant 60 includes a characteristic for which it is desirable to control or limit the coupling forces exerted by coupling assembly 10 on implant 60. For example, implant 60 can be made from a material that can be damaged, deformed, or otherwise undesirably altered when securing member 40 is engaged with receiver member 20 in a manner that sufficiently rigidly fixes anchor 10 in receiver member 20.

Figure 4:
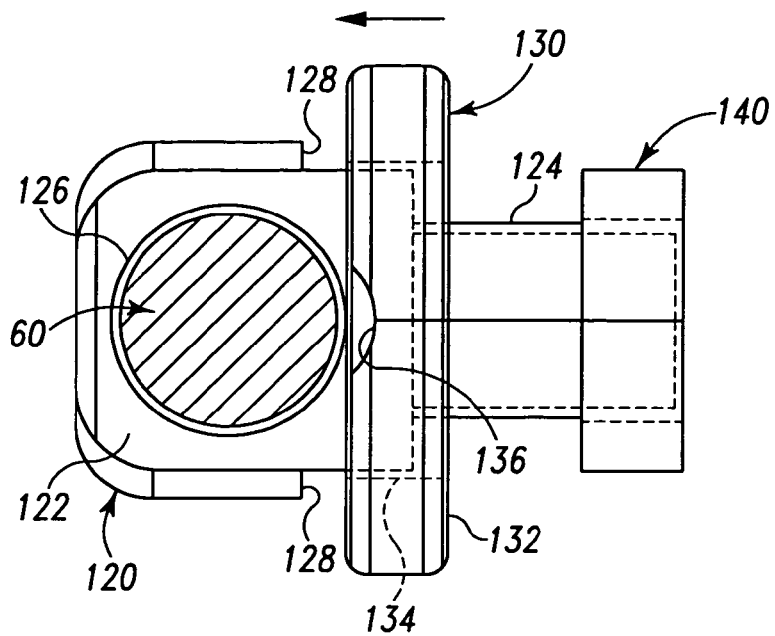
FIG. 4 is an elevation view of another embodiment coupling assembly with the anchor member not shown and with an implant positioned for engagement thereto.
Figure 5:
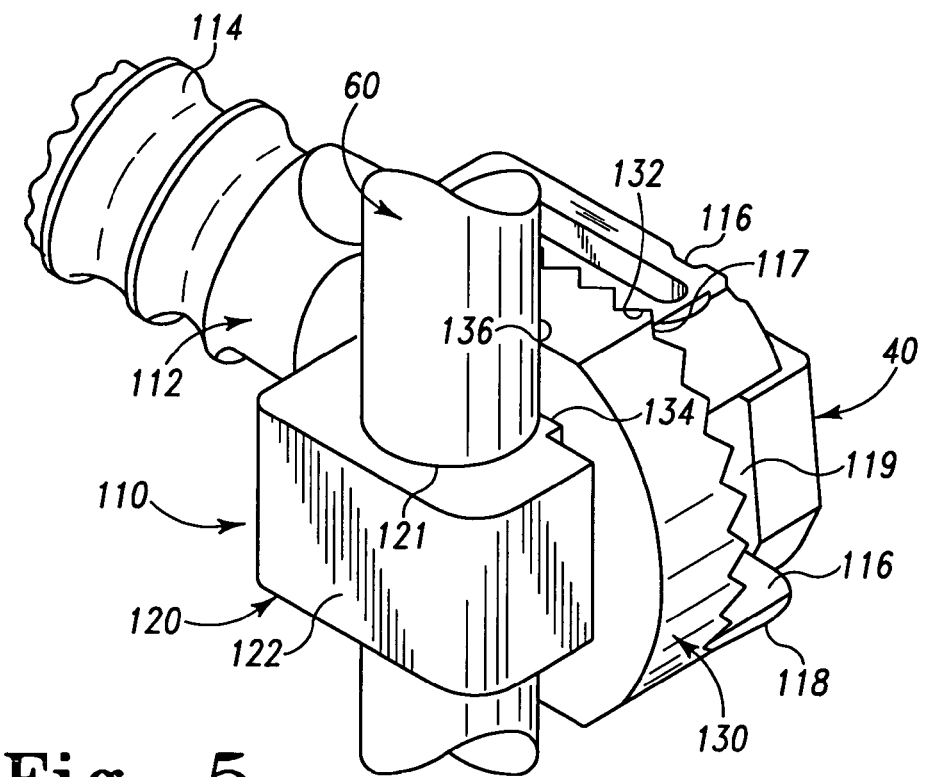
FIG. 5 is a perspective view of the coupling assembly of FIG. 4 with an anchor and an implant engaged thereto.

Referring now to FIGS. 4 and 5, there is shown another embodiment coupling assembly 110 for securing implant 60 along the spinal column. Coupling assembly 110 includes an anchor member 112, a receiver member 120 and a securing member 140. Receiver member 120 includes an implant support surface 121 defined by an implant receiving portion 122. Implant 60 is positioned through implant receiving portion 122. Receiver member 120 further includes an arm 124 extending from receiving portion 122. Arm 124 includes an externally threaded surface profile that threadingly receives securing member 140 thereabout, although other coupling arrangements are also contemplated. In the illustrated embodiment, securing member 140 is a nut. Other embodiments contemplate other forms for securing member 140, including set screws, friction couplings, sleeves, clamps or other devices.

Anchor member 112 includes a threaded shaft 114 and a head 118. Head 118 includes a pair arms 116 spaces from one another to define a passage 119 that receives arm 124 therein. A seat member 130 is positioned adjacent head 118 and implant 60. Seat member 130 defines a central aperture 134 that slidingly receives arm 124 therethrough. The surface of seat member 130 that is adjacent implant 60 includes an implant engaging surface 136 shaped to correspond to the outer surface profile of implant 60 adjacent thereto. The opposite surface of seat member 130 includes grooves 132 that interdigitate and rigidly engage grooves 117 of anchor member head 118 to prevent relative movement between anchor member 112 and the other components of coupling assembly 110 when securing member 140 is firmly positioned against the opposite surface of head 118, as shown in FIG. 5.

Receiver member 120 further provides a force limiting construct in the form of contact surfaces 128 adjacent seat member 130. Contact surfaces 128 project outwardly a sufficient distance from receiving portion 122 so that the surface of seat member 130 adjacent central aperture 134 contacts contact surfaces 128 when positioned adjacent thereto.

Figure 6:
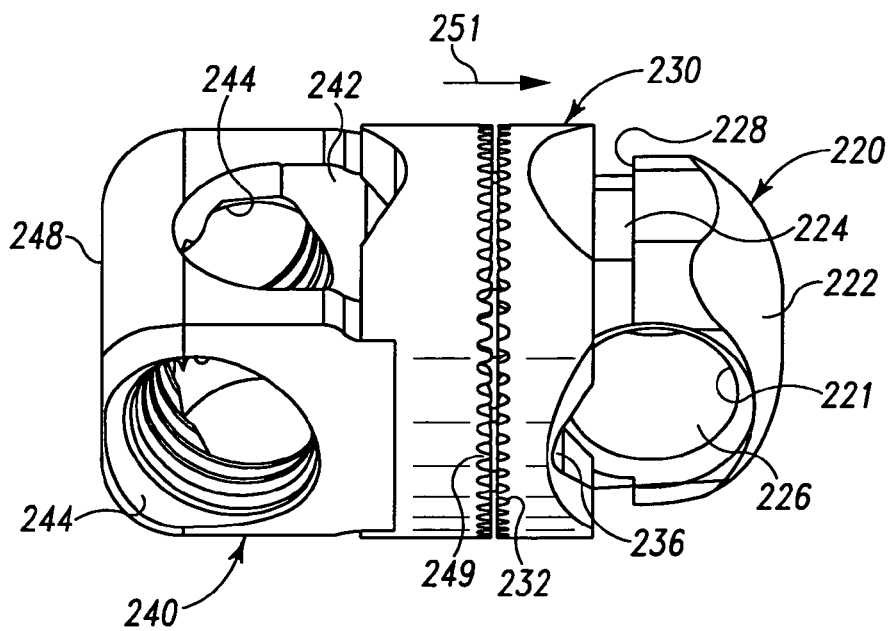
FIG. 6 is a perspective view of another embodiment coupling assembly.
Figure 7:
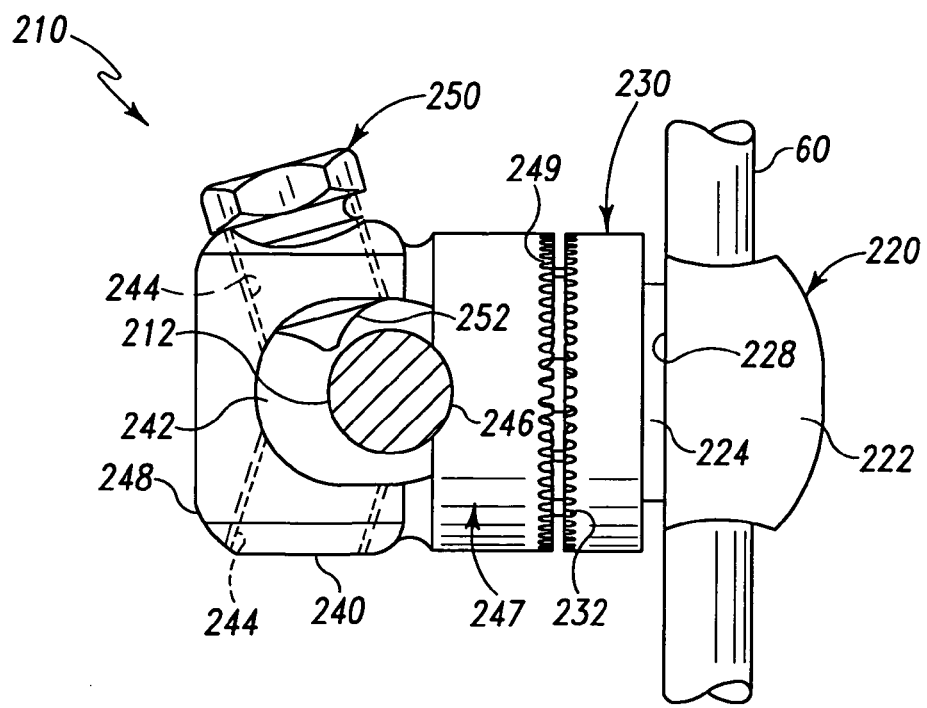
FIG. 7 is an elevational view of the coupling assembly of FIG. 6 with an implant and anchor engaged thereto.

In use, anchor member 112 is engaged to the underlying bony structure. Implant 60 is positioned through implant receiving portion 122, and arm 124 is placed into passage 119 of head 118 of anchor member 112 with seat member 130 on one side of head 118 and securing member 140 on the other side. Securing member 140 is advanced along arm 124 into contact with anchor member 112, and moves seat member 130 and anchor member 12 toward one another. Simultaneously, implant 60 and receiver 120 are moved toward implant engaging surface 136 and into contact therewith. The construct is drawn into firmer engagement until end surface 138 of seat member 130 contacts contact surfaces 128 of receiver member 120. The clamping force exerted on implant 60 between implant support surface 121 and implant engaging surface 136 is thus limited by the force limiting construct of coupling assembly 110. As securing member 140 is further tightened against head 118 of anchor member 112, grooves 117, 132 are positioned into interdigitating contact with one another Referring now to FIGS. 6 and 7, there is shown another embodiment coupling assembly 210 for securing implant 60 along the spinal column. Coupling assembly 210 includes an anchor member 212, a receiver member 220 and at least one securing member 250. Receiver member 220 includes an implant support surface 221 defined by an implant receiving portion 222. Implant 60 is positioned through implant receiving portion 222. Receiver member 220 further includes an arm 224 extending from receiving portion 222. Arm 224 slidingly receives and retains first seat member 230 and second seat member 247 thereabout, although other coupling arrangements are also contemplated.

Opposite implant receiving portion 222, receiver member 220 includes an anchor receiving portion 240. Anchor receiving portion 240 includes a body portion 248 at the opposite end of arm 224. Body portion 248 defines an anchor receptacle 242, and passages 244 extend through and are in communication with anchor receptacle 242. Anchor member 212 includes a proximal end that extends through anchor receptacle 242 of securing member 240. One or more securing members 250 are engaged in respective ones of passages 244, and manipulated to contact anchor member 212 and seat it against an anchor seat 246 of second seat member 247. Further advancement of one or more securing members 250 against anchor member 212 moves first and second seat members 230, 247 toward implant 60, as indicated by arrow 251. If not already so positioned, this positions implant contact surface 236 of seat member 230 in contact with implant 60, and further movement of first seat member 230 in the direction of arrow 251 can be achieved until implant 60 contacts implant support surface 221.

Receiver member 220 further provides a force limiting construct in the form of contact surfaces 228 adjacent seat member 230. Contact surfaces 228 project outwardly a sufficient distance from arm 224 of receiving portion 222 so that the surface of first seat member 230 extending about arm 224 and facing implant 60 contacts contact surfaces 228 when positioned adjacent thereto.

In use, anchor member 212 is engaged to the underlying bony structure. Implant 60 is positioned through implant receiving portion 222, and securing member 250 is manipulated to position anchor member 212 against second seat member 247. This moves implant 60 and anchor member 212 toward one another, resulting in first and second seat members 230, 247 moving relative to one another along arm 224. Further displacement of the assembly with securing member 250 positions first seat member 230 in contact with implant 60, and implant 60 in contact with implant support surface 221 of receiver member 220. First seat member 230 contacts contact surfaces 228, providing a force limiting construct that limits displacement of seat member 230 relative to implant 60 as securing member 250 is further advanced and maintains a minimum spacing between implant engaging surface 236 and implant support surface 221 to limit forces exerted on implant 60. Any further advancement of securing member 250 does not create additional forces on implant 60, and the resulting forces are directed to clamp seat members 230, 247 against one another with the adjacent grooved surfaces in interdigitating, rigid engagement with one another.

In the illustrated embodiment, implant 60 is an elongated spinal rod structured to extend between at least two coupling assemblies to stabilize a motion segment between the at least two coupling assemblies. Various forms for implant 60 are contemplated, including rods, tethers, cables, wires, plates, and staples, for example. In one specific embodiment, implant 60 is a spinal rod comprised of any one or combination of plastic, polymer, tissue, fabric, or mesh material. Other embodiments contemplate that implant 60 can be made from any suitable biocompatible material.

In one technique, the underlying bone forms a portion of a vertebral body of the spinal column. The underlying bone can be a part of the anterior, oblique, antero-lateral, lateral or posterior vertebral elements, including the pedicle, spinous process, transverse processes, lamina or facet, for example. Applications in techniques along any portion or portions of the spinal column are contemplated, including the cervical, thoracic, lumbar and sacral regions. The coupling assemblies and implants can be positioned along the spinal column in invasive procedures where skin and tissue are dissected and retracted to expose the implant locations, or in minimally invasive procedures where one or more the anchor assemblies and implants are guided through at least the tissue adjacent the column to the desired implantation location.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A system for stabilizing a bony segment, comprising:
   an implant;
   a coupling assembly engageable to said implant, wherein said coupling assembly comprises:
      an anchor member engageable to the bony segment;
      a receiver member for receiving the implant; and
      a securing member movable relative to said receiver member to a first position wherein the implant is secured in contact with an implant support surface and an implant engaging surface of said coupling assembly and said coupling assembly provides a compression stress on said implant at said first position, said coupling assembly including a force limiting construct structured to maintain said compression stress exerted on said implant by said coupling assembly when in said first position by providing a minimum spacing between said implant support surface and said implant engaging surface as said securing member and said receiver member are moved relative to one another from said first position with said implant in contact with said implant support surface and said implant engaging surface to a second position to couple said anchor member in said coupling assembly, wherein said force limiting construct includes a seat member in said receiver member positioned between said implant and said anchor member, said seat member including opposite extensions extending at least partially about said implant and said securing member includes opposite extensions extending at least partially about said implant and positionable in contact with said opposite extensions of said seat member at said minimum spacing, the contact between said opposite extensions of said securing member and said seat member preventing movement of said implant support surface and said implant engaging surface toward another.

2. The system of claim 1, wherein:
said anchor member includes a screw having a head pivotally captured in said receiver member; and
said seat member is positioned adjacent said head between said implant and said anchor member, said seat member including said implant support surface and said securing member including said implant engaging surface.

3. The system of claim 2, wherein said securing member includes an engaging portion threadingly engaged to said receiver member and said opposite extensions extend from said engaging portion, wherein said engaging portion is rotatable relative to said opposite extensions so that said opposite extensions linearly advance in said receiver member as said engaging portion is threadingly advanced in said receiver member.

4. The system of claim 3, wherein at the minimum spacing the implant support surface and the implant engaging surface contact the implant, and said securing member is further movable relative to said receiver member to engage said seat member with said head of said anchor member to rigidly fix said anchor member in said receiver member.

5. The system of claim 1, wherein the implant is an elongate spinal rod and said receiver member includes a lower portion for receiving said anchor member and a pair of arms extending from said lower portion, said arms defining an implant receiving portion therebetween for receiving the implant therethrough.

6. The system of claim 5, wherein:
said arms are internally threaded;
said securing member includes an externally threaded body engageable to said arms; and
said implant engaging surface is a concavely curved surface along a distal face of said securing member.

7. The system of claim 1, wherein said receiver member includes an implant receiving portion defining a passage for receiving the implant and an arm extending from said implant receiving portion, said implant support surface extending along at least a portion of said passage.

8. The system of claim 7, wherein said receiver member includes an anchor receiving portion opposite said implant receiving portion, said anchor receiving portion defining a passage for receiving a proximal end of said anchor member, said seat member being positionable in contact with said proximal end of said anchor member to secure said receiver member to said anchor member.

9. The system of claim 1, wherein the bony segment is a spinal column.

10. A coupling assembly for securing an implant along a spinal column, comprising:
an anchor member engageable to the spinal column;
a receiver member including an anchor receiving portion for receiving the anchor member and an implant receiving portion for receiving the implant;
at least one seat member movable relative to said receiver member, said at least one seat member including an implant support surface; and
a securing member with an engaging portion engaged with said receiver member and opposite extensions extending from said engaging portion toward said at least one seat member, said opposite extensions defining an implant engaging surface extending therebetween, said engaging portion being rotatable relative to said opposite extensions so that said opposite extensions are linearly moved in said receiver member as said engaging portion is advanced into said receiver member to contact said opposite extensions with said at least one seat member and move said at least one seat member to a first position to engage the implant in contact with said implant support surface and said implant engaging surface with said implant support surface and said implant engaging surface separated by a distance that exerts a compression stress on said implant, said securing member being movable to a second position to rigidly engage said anchor member with said receiver member while maintaining said distance to maintain the compression stress exerted on said implant during movement of said securing member to said second position wherein said opposite extensions of said securing member include contact surfaces contacting said seat member in said first position to prevent said seat member from moving toward the implant from said first position.

11. The assembly of claim 10, wherein:
said anchor member includes a screw having a head pivotally captured in said receiver member; and
said seat member is positioned adjacent said head between the implant and said anchor member.

12. The assembly of claim 10, wherein said engaging portion of said securing member is threadingly engaged to said receiver member, wherein said engaging portion is rotatable relative to said opposite extensions so that said opposite extensions linearly advance in said receiver member as said engaging portion is threadingly advanced in said receiver member.

13. The assembly of claim 10, wherein at the minimum spacing said implant support surface and said implant engaging surface contact the implant, and said securing member is further movable relative to said receiver member to engage said seat member with said anchor member to rigidly fix said anchor member in said receiver member.

14. The assembly of claim 10, wherein said receiver member includes a lower portion for receiving said anchor member and a pair of arms extending from said lower portion, said arms defining said implant receiving portion therebetween for receiving the implant therethrough.

15. The assembly of claim 14, wherein:
said arms are internally threaded;
said securing member includes an externally threaded body engageable to said arms; and
said implant engaging surface is a concavely curved surface along a distal face of said securing member.

16. The assembly of claim 10, wherein said implant receiving portion of said receiver member defines a passage for receiving the implant and an arm extending from said implant receiving portion, said implant support surface extending along at least a portion of said passage.

17. A coupling assembly for engaging an implant along a spinal column, the coupling assembly comprising:
an anchor member engageable to the spinal column;
a receiver member including an implant receiving portion for receiving the implant;
a seat member positioned in the receiver member adjacent said anchor member, said seat member including an implant support surface facing away from said anchor member; and
a securing member including an engaging portion engageable to said receiver member and opposite extensions extending from said engaging portion toward said seat member, said securing member including an implant engaging surface extending between said opposite extensions oriented toward said implant support surface, said engaging portion of said securing member being movable relative to both said opposite extensions and said receiver member to a first position to secure the implant between said implant support surface and said implant engaging surface, wherein in said first position said opposite extensions of said securing member contact said seat member when the implant is positioned between the securing member and the seat member to maintain a minimum spacing between said implant support surface and said implant engaging surface as said securing member is advanced in said receiver member to move said seat member in contact with said anchor member to rigidly couple said anchor member in said receiver member.

18. The assembly of claim 17, wherein:
said anchor member includes a screw having a head pivotally captured in said receiver member; and
said seat member is positioned adjacent said head between the implant and said anchor member.

19. The assembly of claim 17, wherein said engaging portion of said securing member is threadingly engaged to said receiver member, wherein said engaging portion is rotatable relative to said opposite extensions so that said opposite extensions linearly advance in said receiver member as said engaging portion is threadingly advanced in said receiver member.

20. The assembly of claim 17, wherein at the minimum spacing said implant support surface and said implant engaging surface contact the implant, and said securing member is further movable relative to said receiver member to engage said seat member with said anchor member to rigidly fix said anchor member in said receiver member.

21. The assembly of claim 17, wherein said receiver member includes a lower portion for receiving said anchor member and a pair of arms extending from said lower portion, said arms defining said implant receiving portion therebetween for receiving the implant therethrough.

22. The assembly of claim 21, wherein:
said arms are internally threaded;
said securing member includes an externally threaded body engageable to said arms; and
said implant engaging surface is a concavely curved surface along a distal face of said securing member formed by said opposite extensions.

23. The assembly of claim 17, wherein said implant receiving portion of said receiver member defines a passage for receiving the implant and an arm extending from said implant receiving portion, said implant support surface extending along at least a portion of said passage.

* * * * *